(12) United States Patent
Wagman

(10) Patent No.: US 7,108,722 B2
(45) Date of Patent: Sep. 19, 2006

(54) PROSTHETIC ATTACHMENT LOCKING DEVICE WITH DUAL LOCKING MECHANISM

(75) Inventor: Chris L. Wagman, Red Lion, PA (US)

(73) Assignee: Wagman Manufacturing, Inc., Manchester, PA (US)

( * ) Notice: Subject to any disclaimer, the term of this patent is extended or adjusted under 35 U.S.C. 154(b) by 215 days.

(21) Appl. No.: 10/810,519

(22) Filed: Mar. 26, 2004

(65) Prior Publication Data

US 2005/0216096 A1    Sep. 29, 2005

(51) Int. Cl.
*A61F 2/80*    (2006.01)
(52) U.S. Cl. ..................................... 623/38
(58) Field of Classification Search ............ 623/33–36, 623/38; 403/344, 105
See application file for complete search history.

(56) References Cited

U.S. PATENT DOCUMENTS

| | | | |
|---|---|---|---|
| 5,226,918 A | 7/1993 | Silagy et al. ................. | 623/32 |
| 5,507,837 A | 4/1996 | Laghi ........................... | 623/38 |
| 5,662,715 A | 9/1997 | Slemker ....................... | 623/36 |
| 5,888,234 A | 3/1999 | Littig ........................... | 623/38 |
| 6,051,026 A | 4/2000 | Biedermann et al. ......... | 623/38 |
| 6,106,559 A | 8/2000 | Meyer .......................... | 623/33 |
| 6,267,787 B1 | 7/2001 | Capper et al. ................ | 623/36 |
| 6,334,876 B1 | 1/2002 | Perkins ........................ | 623/34 |
| 6,361,569 B1 | 3/2002 | Slemker et al. .............. | 623/33 |
| 6,440,173 B1* | 8/2002 | Meyer .......................... | 623/36 |
| 6,596,028 B1* | 7/2003 | Laghi .......................... | 623/33 |
| 6,605,118 B1 | 8/2003 | Capper et al. ................ | 623/36 |
| 6,626,951 B1* | 9/2003 | Gramnas ...................... | 623/33 |
| 6,893,468 B1* | 5/2005 | Lund ........................... | 623/36 |
| 6,979,354 B1* | 12/2005 | Wagman ...................... | 623/33 |

\* cited by examiner

*Primary Examiner*—Alvin J. Stewart
(74) *Attorney, Agent, or Firm*—Barley Snyder LLC

(57) ABSTRACT

A prosthetic attachment locking device includes a body and a locking mechanism. The body has an axial hole that extends between a first surface and a second surface. The locking mechanism has a central axle with a pawl that communicates with the axial hole. The pawl is displaceable to selectively engage with an attachment pin received in the axial hole. The locking mechanism has a one-way clutch and a ratchet. The one-way clutch and the ratchet are formed to receive the central axle and permit one-way rotation of the pawl.

27 Claims, 11 Drawing Sheets

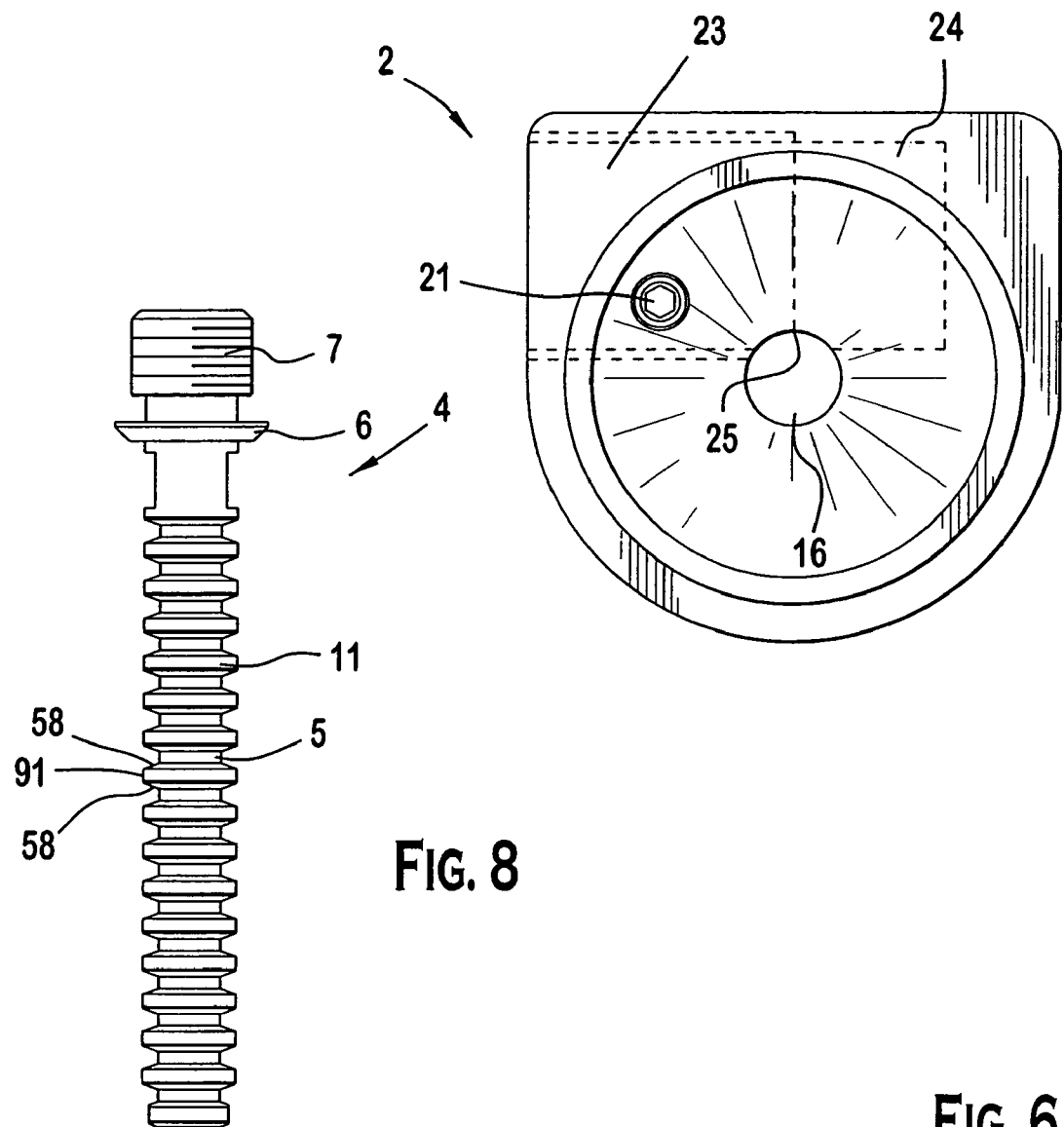
FIG. 5
FIG. 8
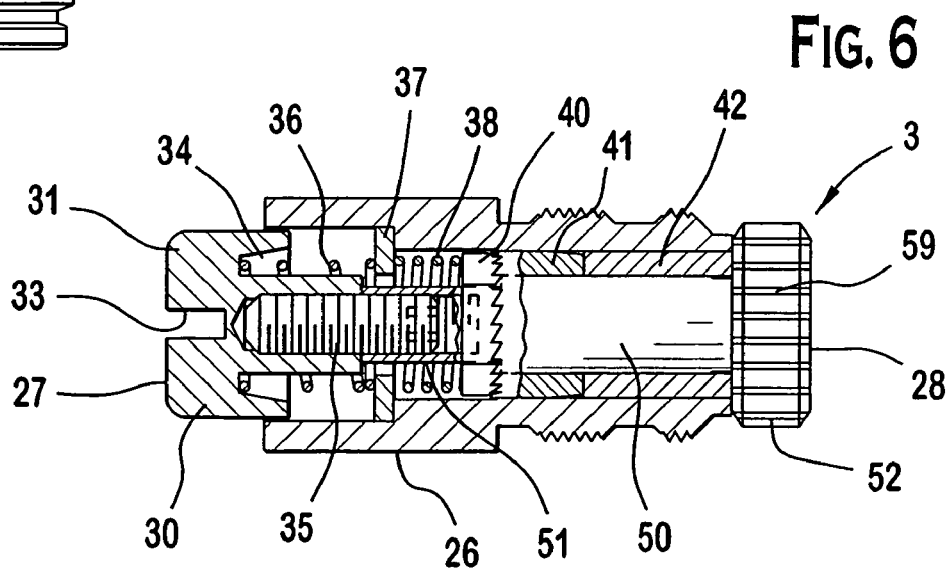
FIG. 6

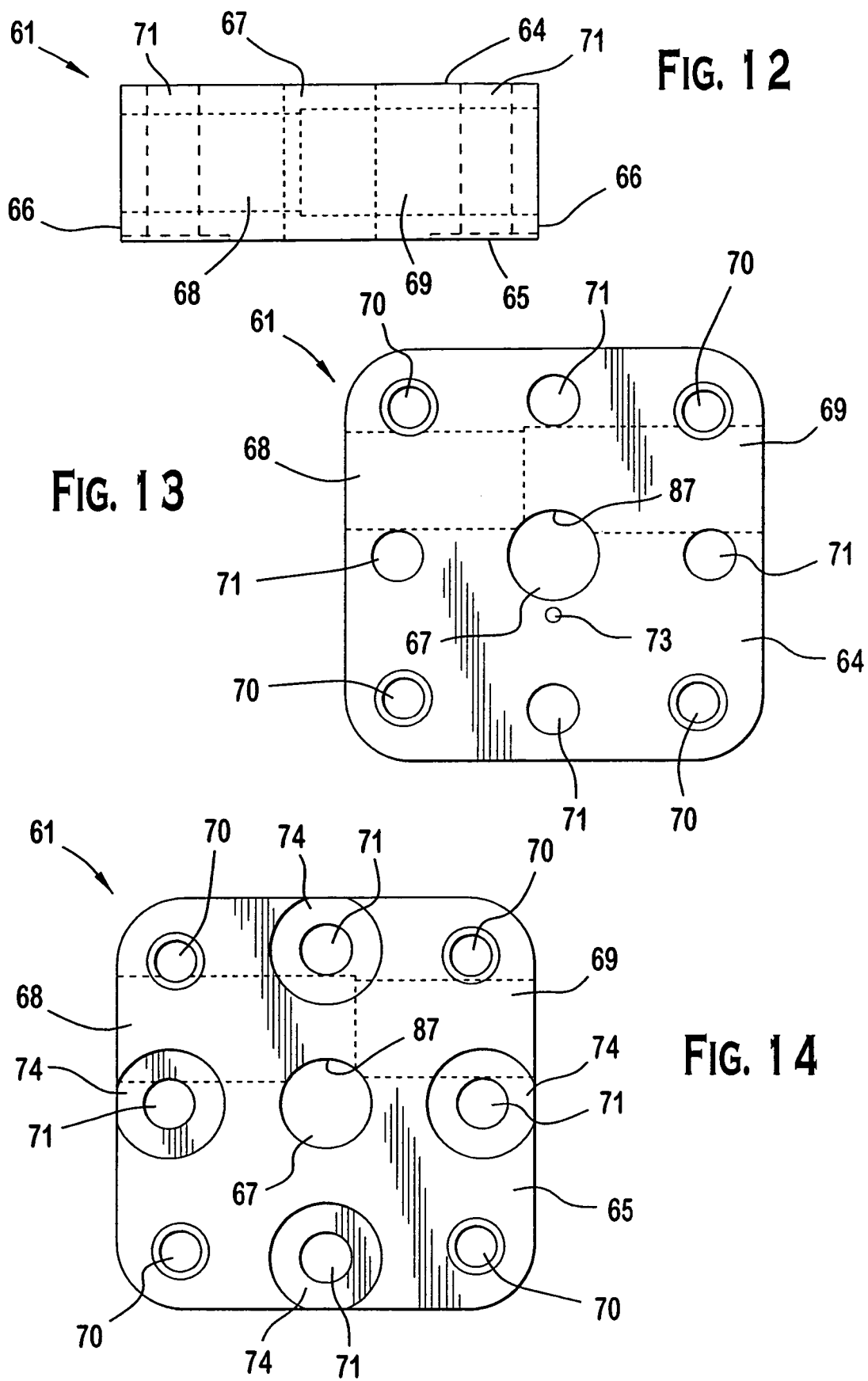

PROSTHETIC ATTACHMENT LOCKING DEVICE WITH DUAL LOCKING MECHANISM

FIELD OF THE INVENTION

The invention relates to a prosthetic attachment locking device and, more specifically, to a prosthetic attachment locking device with a dual locking mechanism.

BACKGROUND OF THE INVENTION

Prosthetic attachment locking devices are used to secure a residual limb, which has been fitted in a socket, to a pylon of a prosthetic limb. The prosthetic attachment locking device generally includes a body having an axial hole extending therethrough and a locking mechanism having a spring loaded reciprocating pawl that cooperates with the axial hole. The socket has a socket adapter that is attached to a first surface of the body by a fastening means that is passed through a set of through-holes in the body. An attachment pin that extends from a liner positioned about the residual limb is inserted through the socket adapter and through the axial hole of the prosthetic attachment locking device until a distal end of the attachment pin is received in the pylon of the prosthetic limb. As the attachment pin is inserted, ratcheted teeth of the attachment pin engage with teeth of the pawl. Because the pawl rotates in only one direction, the attachment pin becomes locked in the body and secures the residual limb to the prosthetic limb. To release the attachment pin from the body, the pawl is displaced from the axial hole so that the pawl disengages from the attachment pin. The attachment pin is then removed from the body to unsecure the residual and prosthetic limbs.

Because many prosthetic attachment locking devices use either a one-way clutch or a ratchet to limit the rotation of the pawl to a single direction, if the attachment pin reaches a point of complete insertion in-between locking positions, a certain amount of play can occur between the pawl and the attachment pin. Additionally, the ratcheted teeth of the attachment pin are generally rounded and do not completely mesh with the teeth of the pawl, which can cause a certain amount of play to occur between the ratcheted teeth of the attachment pin and the teeth of the pawl. Because any type of play that occurs between the attachment pin and the pawl causes the prosthetic limb to move in relation to the residual limb during use, a user may experience discomfort and/or the attachment pin may become loosened from its locked position within the body. Further, the body receiving surface of the socket adapter is often irregular as a result of grinding during the fabrication process. The irregular body receiving surface can cause further discomfort to the user.

SUMMARY OF THE INVENTION

The invention relates to a prosthetic attachment locking device having a body and a locking mechanism. The body has an axial hole that extends between a first surface and a second surface. The locking mechanism has a central axle with a pawl that communicates with the axial hole. The pawl is displaceable to selectively engage with an attachment pin received in the axial hole. The locking mechanism has a one-way clutch and a ratchet. The one-way clutch and the ratchet are formed to receive the central axle and permit one-way rotation of the pawl.

The invention further relates to a locking mechanism for a prosthetic attachment locking device. The locking mechanism includes a central axle having a pawl. A one-way clutch rotatably mounts the central axle and permits one-way rotation of the central axle. A ratchet non-rotatably mounts the central axle and permits one-way rotation of the central axle. A release button is attached to the central axle and is biased by a first compression spring. The release button is moveable to displace the central axle and the pawl.

BRIEF DESCRIPTION OF THE DRAWINGS

FIG. 5 is a top schematic view of the body of the prosthetic attachment locking device of FIG. 1.

FIG. 6 is a cross-sectional side view of a locking mechanism of the prosthetic attachment locking device of FIG. 1.

FIG. 8 is a front view of an attachment pin of the prosthetic attachment locking device of FIG. 1.

FIG. 12 is a cross-sectional side view of a body of the prosthetic attachment locking device of FIG. 10.

FIG. 13 is a top schematic view of the body of the prosthetic attachment locking device of FIG. 10.

FIG. 14 is a bottom schematic view of the body of the prosthetic attachment locking device of FIG. 10.

DETAILED DESCRIPTION OF THE PREFERRED EMBODIMENT

Figure 1:
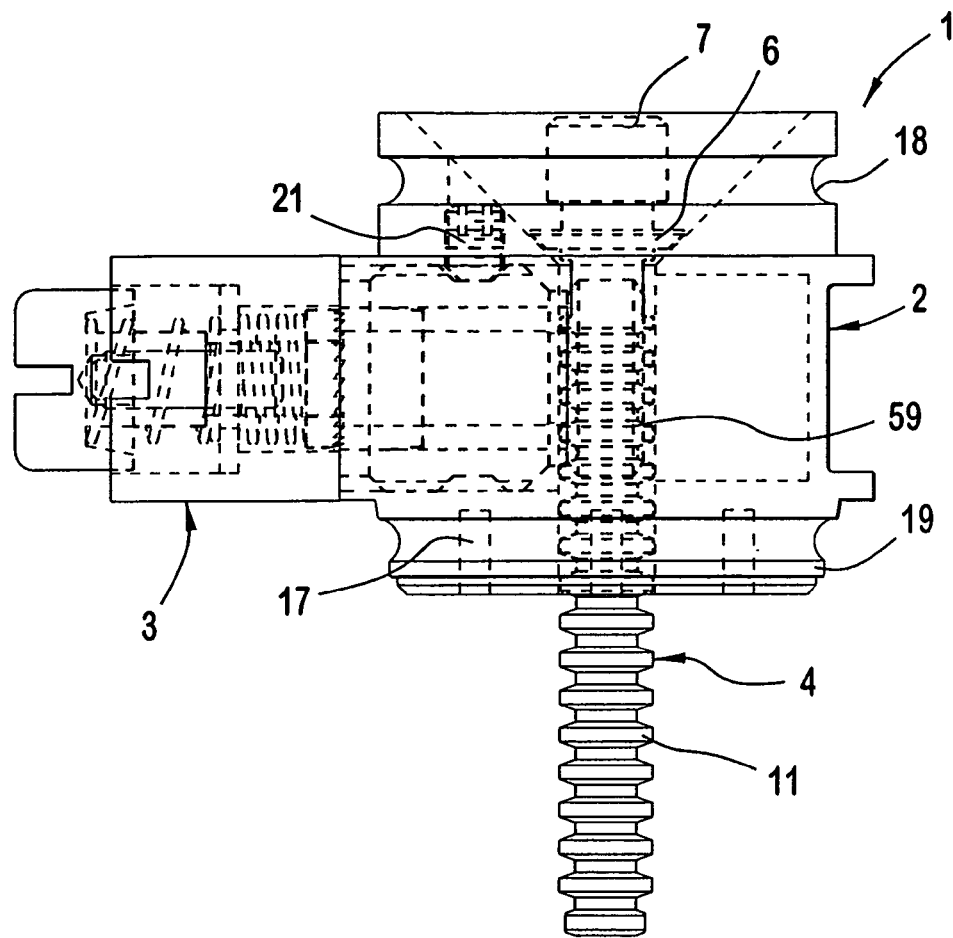
FIG. 1 is a schematic side view of a first embodiment of a prosthetic attachment locking device according to the invention.
Figure 2:
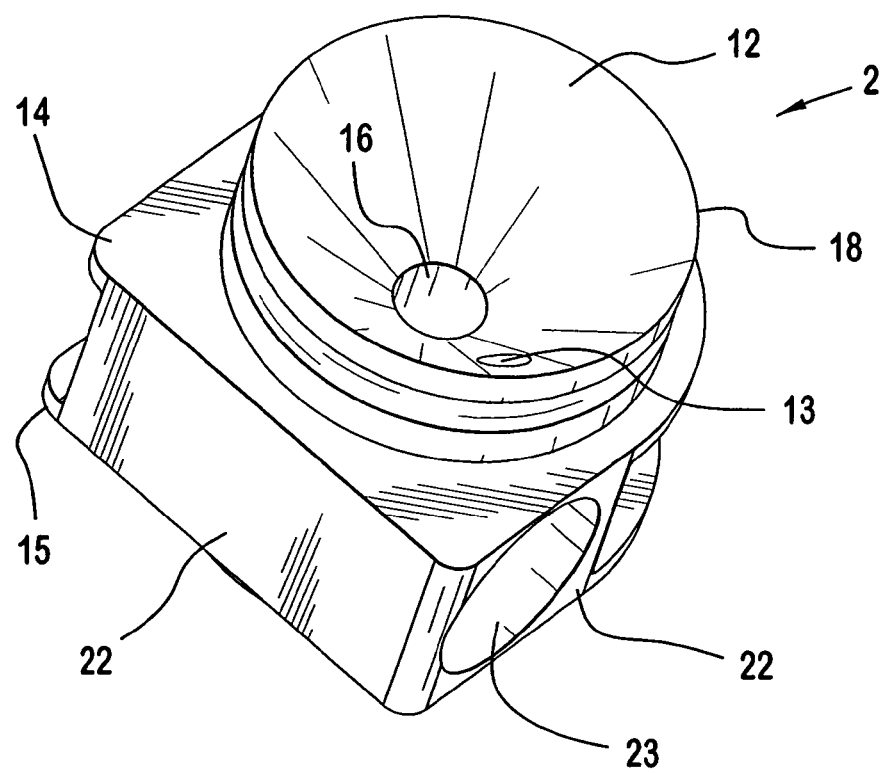
FIG. 2 is a perspective view of a body of the prosthetic attachment locking device of FIG. 1.
Figure 3:
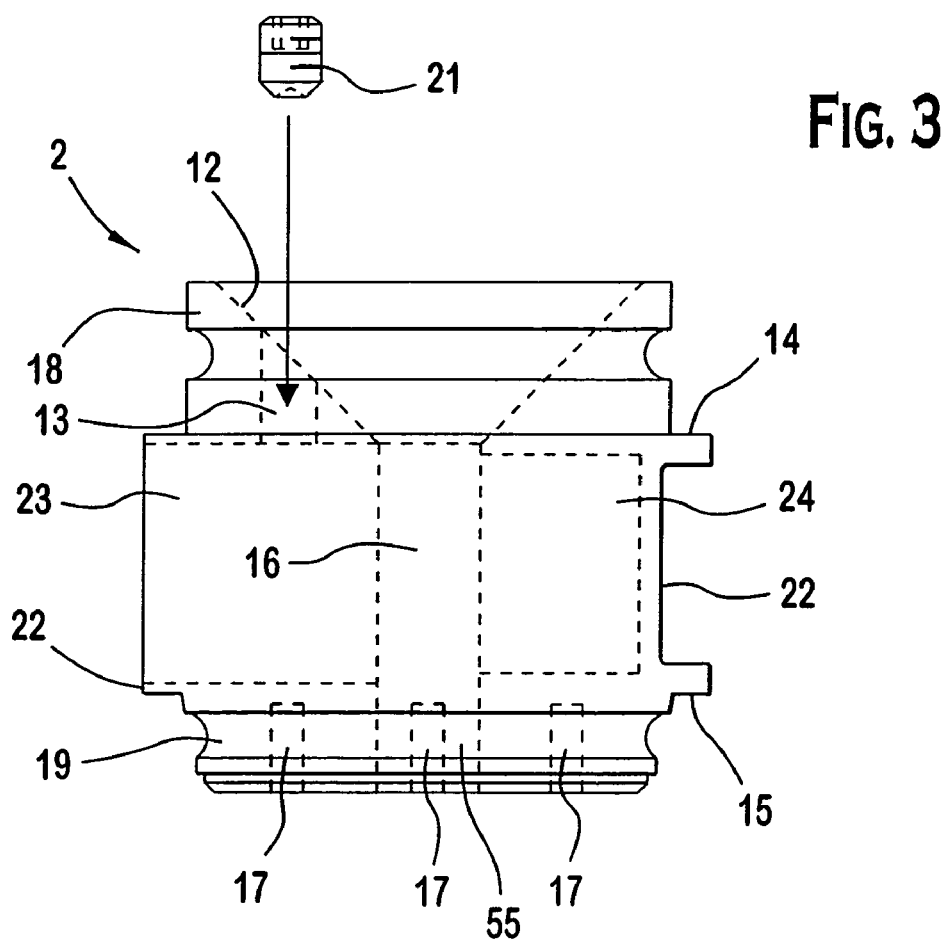
FIG. 3 is a schematic side view of the body of the prosthetic attachment locking device of FIG. 1.

FIGS. 1–9 show a first embodiment of a prosthetic attachment locking device 1. As shown in FIG. 1, the prosthetic attachment locking device I comprises a body 2 with an integral socket adapter 18, a locking mechanism 3, and an attachment pin 4. As shown in FIGS. 2 and 3, the body 2 has side surfaces 22 extending between essentially planar first and second surfaces 14, 15. An axial hole 16 is formed in an approximate center of the body 2 and extends from the first surface 14 to the second surface 15. Extending from one of the side surfaces 22 of the body 2 toward the axial hole 16 is a threaded sleeve receiving recess 23. Adjacent to the sleeve receiving recess 23 is a pawl receiving recess 24. The pawl receiving recess 24 has a diameter smaller than the sleeve receiving recess 23 and extends from the sleeve receiving recess 23 away from the axial hole 16. As shown in FIG. 5, a portion of the sleeve receiving recess 23 and the pawl receiving recess 24 communicate with the axial hole 16 to form a pawl receiving slot 25.

Figure 4:
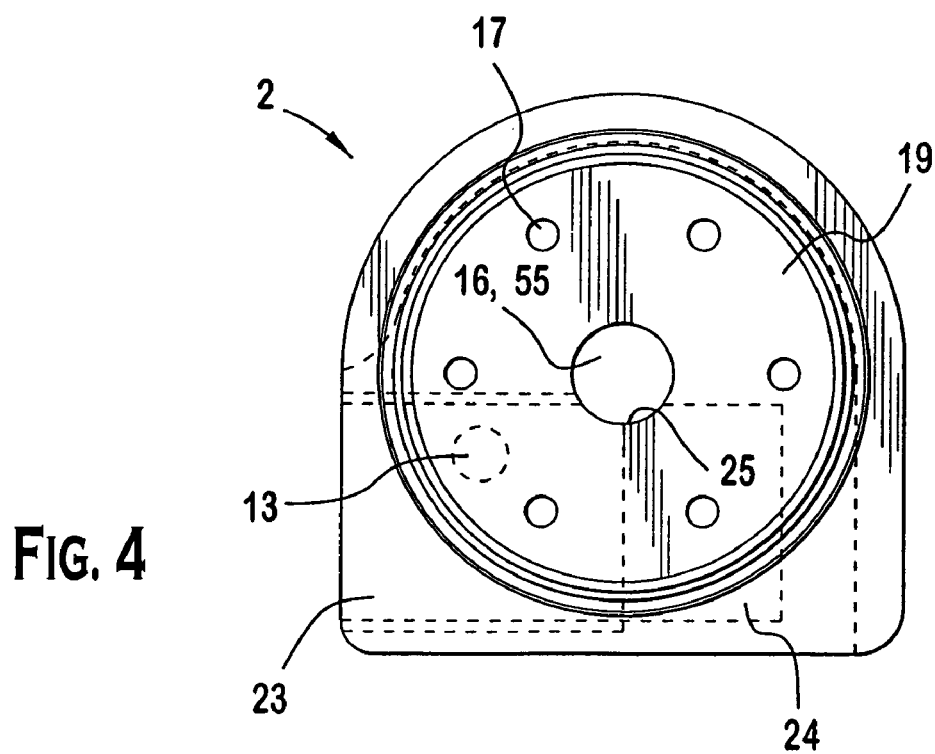
FIG. 4 is a bottom schematic view of the body of the prosthetic attachment locking device of FIG. 1.

As shown in FIGS. 2 and 3, the socket adapter 18 is integrally formed with the first surface 14 of the body 2. The socket adapter 18 is essentially cone-shaped and has an outer surface 12 that tapers inward proximate the axial hole 16. As shown in FIG. 3, a recess 13 for receipt of a locking mechanism 21, such as a screw, extends from the outer surface 12 to the sleeve receiving recess 23. A prosthetic receiving portion 19 is integrally formed with the second surface 15 of the body 2. The prosthetic receiving portion 19 has an attachment pin receiving aperture 55 corresponding to the axial hole 16. As shown in FIG. 4, a first set of through-holes 17 are formed in the prosthetic receiving portion 19 and are arranged to encompass the axial hole 16. The first set of through-holes 17 may be threaded and form a universal pattern for attachment of the body 2 to a pylon 8 of a prosthetic limb (not shown), to be described later, by a fastening means (not shown), such as a screw.

Figure 9:
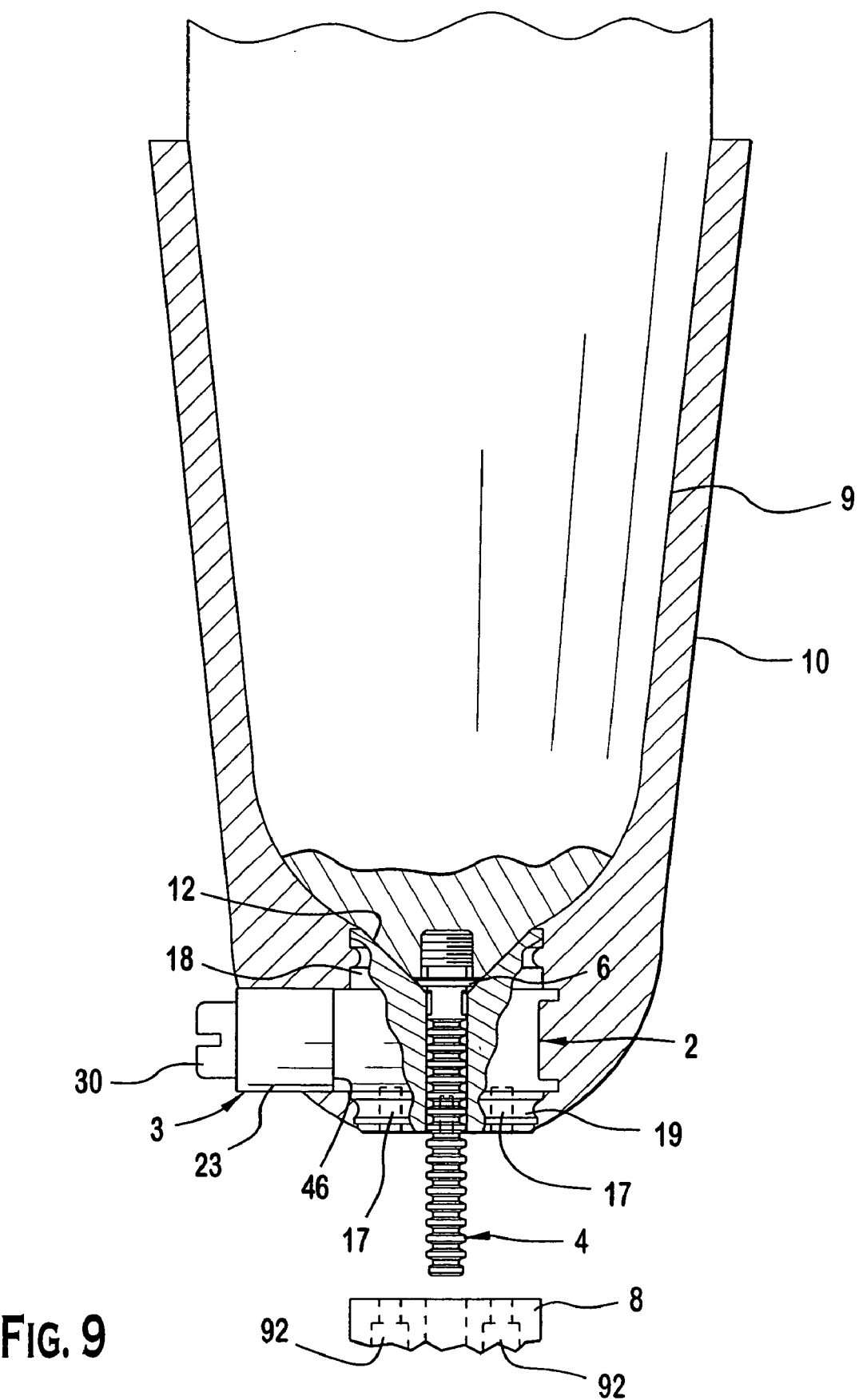
FIG. 9 is an exploded view of the prosthetic attachment locking device of FIG. 1 attached to a residual limb.

The body 2 may be molded from a plastic material, such as DELRIN, for light weight and durability. Alternatively, the body 2 may be machined from other suitable materials, such as, aluminum or titanium. The socket adapter 18 and the prosthetic receiving portion 19 may be integrally molded with the body 2 or laminated thereto. As shown in FIG. 9, the socket adapter 18 and/or the body 2 may also be laminated with a conventional socket 10, to be described later, or vacuum formed therein.

Figure 7:
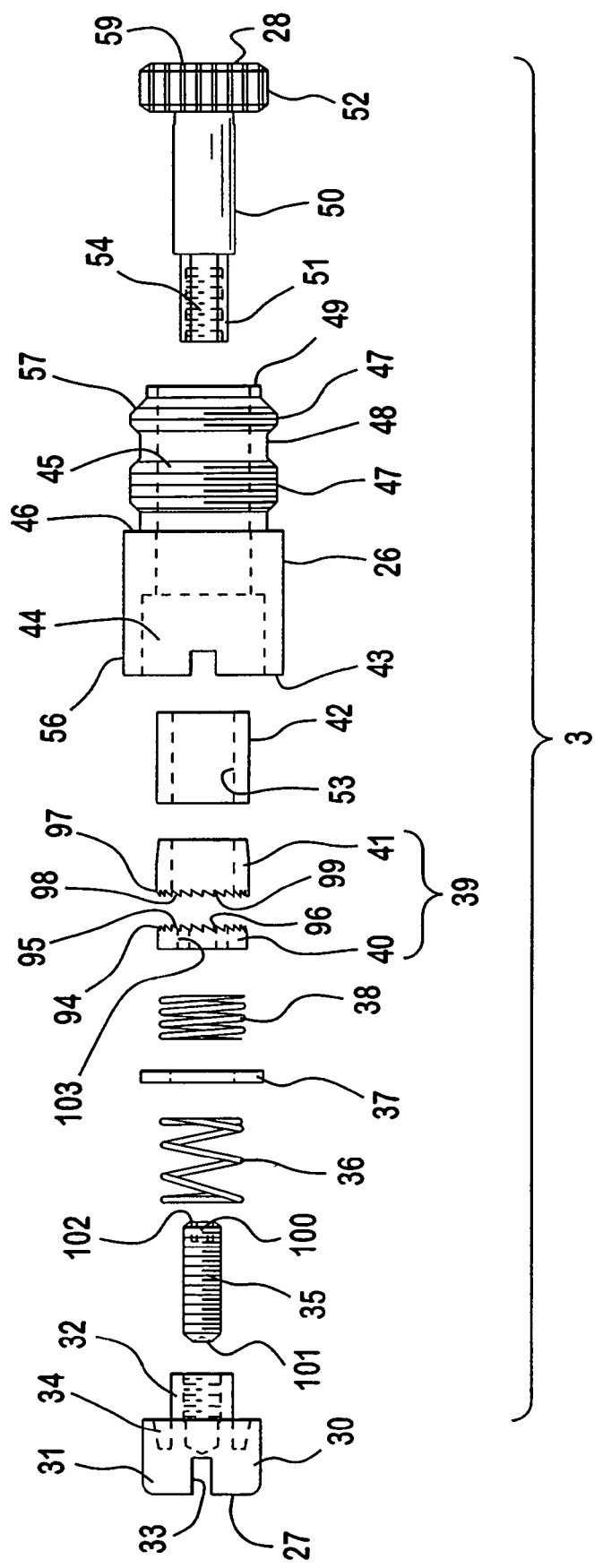
FIG. 7 is an exploded view of the locking mechanism of the prosthetic attachment locking device of FIG. 1.

As shown in FIG. 6, the locking mechanism 3 is essentially cylindrical in shape and has a first end 27 and a second end 28. The locking mechanism 3 may be made from a material such as a high strength aluminum alloy for light weight and durability. As shown in FIG. 7, the first end 27 of the locking mechanism 3 has a release button 30. The release button 30 includes a head 31 with a hollow shaft 32 extending therefrom. The hollow shaft 32 has a smaller diameter than the head 31. On a side opposite from the hollow shaft 32, the head 31 has an elongated recess 33 formed for receipt of a tool (not shown), such as a screwdriver. A first end 101 of a screw 35 is received in the hollow shaft 32 that extends from the hollow shaft 32 toward the second end 28. The screw 35 has a second end 102 provided with an attachment means 100, such as a hex screw, that attaches the screw 35 to the release button 30. In the alternative, the screw 35 may be integrally formed with the hollow shaft 32 and/or the head 31. Proximate the hollow shaft 32, the head 31 is formed with an undercut 34. The undercut 34 encompasses the hollow shaft 32 and is formed for receipt of a first compression spring 36 that is positioned about the hollow shaft 32 and the screw 35, as shown in FIG. 6. In the alternative, the head 31 could be formed without an undercut 34, and the first compression spring 36 could rest on the substantially planar surface of the head 31 proximate the hollow shaft 32.

As shown in FIG. 6, adjacent to the release button 30 is a sleeve 26. As shown in FIG. 7, the sleeve 26 is substantially cylindrical in shape and has a first face 43 and a second face 49. A button receiving recess 44 extends from the first face 43 toward the second face 49. Adjacent to the button receiving recess 44 is a clutch receiving recess 45. The clutch receiving recess 45 extends from the button receiving recess 44 through the second face 49. An outer surface of the sleeve 26 is formed to have a first half 56 with an abutment surface 46 and a second half 57 with a threaded surface 47. In an approximate middle of the threaded surface 47 is a locking surface 48.

As shown in FIGS. 6 and 7, a spacer 37 is arranged in the button receiving recess 44. A second compression spring 38 or disc spring is arranged adjacent to the spacer 37 and in the clutch receiving recess 45. The second compression spring 38 may have a lighter compression threshold than the first compression spring 36. A ratchet 39 is arranged adjacent to the second compression spring 38 and in the clutch receiving recess 45. The ratchet 39 consists of a driving portion 40 and a stationary portion 41. The driving portion 40 has a substantially hexagonal inner surface 103 or, alternatively, two flat inner surfaces (not shown) and a plurality of driving teeth 94 extending toward the stationary portion 41. Each of the driving teeth 94 consists of an angled surface 95 and an orthogonal surface 96. The stationary portion 41 has a plurality of stationary teeth 97 corresponding to and extending toward the driving portion 40. Each of the stationary teeth 97 consists of an angled surface 98 and an orthogonal surface 99 corresponding to the angled surface 95 and the orthogonal surface 96 of the driving teeth 94. As shown in FIG. 6, the driving portion 40 is positioned adjacent to the second compression spring 38. The stationary portion 41 is positioned adjacent to the driving portion 40 and may be integrally formed with sleeve 26. A one-way clutch 42 is arranged adjacent to the stationary portion 41 and in the clutch receiving recess 45. The one-way clutch 42 has an inner sleeve 53 that forms a bearing for a central axle 50 and is formed to permit rotation of the central axle 50 in a single direction. In the alternative, the second compression spring 38 and the spacer 37 could be eliminated, and the first compression spring 36 could be arranged adjacent to the driving portion 40.

As shown in FIG. 7, at the second end 28 of the locking mechanism 3 is the central axle 50. The central axle 50 has an attachment end 51 and a pawl 52. The attachment end 51 has a screw receiving recess 54 and a substantially hexagonal outer surface or, alternatively, two flat outer surfaces (not shown) that corresponds with the inner surface 103 of the driving portion 40. The pawl 52 has a plurality of teeth 59 formed for engaging the attachment pin 4. The pawl 52 may be, for example, a spur gear with the teeth 59 arranged at a medium pitch and a pressure angle of approximately 20 degrees.

As shown in FIG. 8, the attachment pin 4 has a pin body 5, a pin head 7, and a lip 6. The lip 6 has a larger diameter then the pin head 7 and is positioned between the pin head 7 and the pin body 5. The pin body 5 has a plurality of ratcheted teeth 11 that extend a length of the pin body 5. Each of the ratcheted teeth 11 has a substantially flat engaging surface 58. Each of the ratcheted teeth 11 has a depth from an outer circumference 91 thereof to the pin body 5 of approximately 1/16 of an inch to correspond with the teeth 59 of the pawl 52. The attachment pin 4 may be made from a material such as a high strength stainless alloy for corrosive resistance and durability.

The assembly and operation of the first embodiment of the prosthetic attachment locking device 1 will now be described in greater detail with reference to FIGS. 1, 6, and 9. As shown in FIG. 6, to assemble the locking mechanism 3, the attachment end 51 of the central axle 50 is inserted into the second face 49 of the sleeve 26 until the attachment end 51 is received in the driving portion 40 and the pawl 52 abuts the second face 49. The release button 30 is inserted into the button receiving recess 44 so that the screw 35, which is encompassed with the first compression spring 36, is received by the spacer 37 and the second compression spring 38. The screw 35 is secured in the screw receiving recess 54 of the attachment end 51 by rotating the release button 30 either manually or with a tool (not shown) positioned in the recess 33. The release button 30, the sleeve 26, and the central axle 50 are thereby attached to form a single unit. In the assembled state, the release button 30 is biased by the first compression spring 36 toward the first end 27, and the driving portion 40 is biased by the second compression spring 38 toward the second end 28 and against the driving portion 40.

As shown in FIGS. 1 and 9, the second end 28 of the assembled locking mechanism 3 is inserted into the button receiving recess 23 of the body 2. The second half 57 of the sleeve 26 is screwed into the button receiving recess 23 until the abutment surface 46 of the first half 56 engages the side surface 22 of the body 2. In this position, the pawl 52 is positioned in the pawl receiving recess 24 and communicates with the pawl receiving slot 25. The locking mechanism 21, which may be a screw, is screwed into the recess 13 from the outer surface 12 of the socket adapter 18 to abut the locking surface 48 of the sleeve 26. The locking mechanism 21 thereby secures the locking mechanism 3 in the body 2.

The prosthetic receiving portion 19 is positioned adjacent to the pylon 8 of the prosthetic limb (not shown). Fastening means (not shown), such as screws, that extend from apertures 92 in the pylon 8 are received in the first set of through-holes 17 in the prosthetic receiving portion 19. The fastening means (not shown) attach the pylon 8 and the prosthetic limb (not shown) to the body 2.

The conventional socket 10, which has been laminated or vacuum formed with the socket adapter 18, is fitted over a liner 9 that covers a residual limb (not shown). As the conventional socket 10 is positioned over the liner 9, the attachment pin 4, which extends from the liner 9, is guided into the axial hole 16 by the outer surface 12 of the socket adapter 18. As the attachment pin 4 is received in the axial hole 16, the ratcheted teeth 11 of the attachment pin 4 engage the teeth 59 of the pawl 52 at the pawl receiving slot 25 and cause the central axle 50 to rotate within the one-way clutch 42. The rotation of the central axle 50 causes the driving portion 40 to rotate with the attachment end 51. As the driving portion 40 rotates, the ratchet 39 locks in discrete positions, and the driving teeth 94 engage the stationary teeth 97 to cause an audible clicking sound. The attachment pin 4 is inserted until the lip 6 of the attachment pin 4 is positioned adjacent to the axial hole 16 and a distal end of the attachment pin 4 is received in the pylon 8 of the prosthetic limb (not shown) to secure the residual limb (not shown) to the prosthetic limb (not shown).

To detach the liner 9 of the residual limb (not shown) from the prosthetic limb (not shown), the head 31 of the release button 30 is pressed toward the body 2 and against the bias of the first compression spring 36. As the head 31 is received in the button receiving recess 44 of the sleeve 23, the head 31 displaces the central axle 50 and the pawl 52. The abutment surface 46 and the locking mechanism 21 hold the sleeve 26 in position while the central axle 50 and pawl 52 are being displaced. The pawl 52 is displaced beyond the pawl receiving slot 25 so that the attachment pin 4 is released from the pawl 52 and resultantly may be removed from the axial hole 16 to detach the liner 9 of the residual limb (not shown) from the prosthetic limb (not shown).

Because the attachment pin 4 is secured in the body 2 by the driving portion 40 engaging with the stationary portion 41 and the central axle 50 engaging with the one-way clutch 42, the attachment pin 4 is dually locked in the body 2 and play between the attachment pin 2 and the pawl 52 is reduced. Additionally, because the ratcheted teeth 11 of the attachment pin 4 are substantially flat, the teeth 59 of the pawl 52 mesh with the ratcheted teeth 11 of the attachment pin 4 to reduce play between the ratcheted teeth 11 and the teeth 59. Further, the socket adapter 18 is integrally formed with the body 2 and thereby eliminates the uneven distribution of torque that occurs with a conventional socket adapter.

Figures 10, 11:
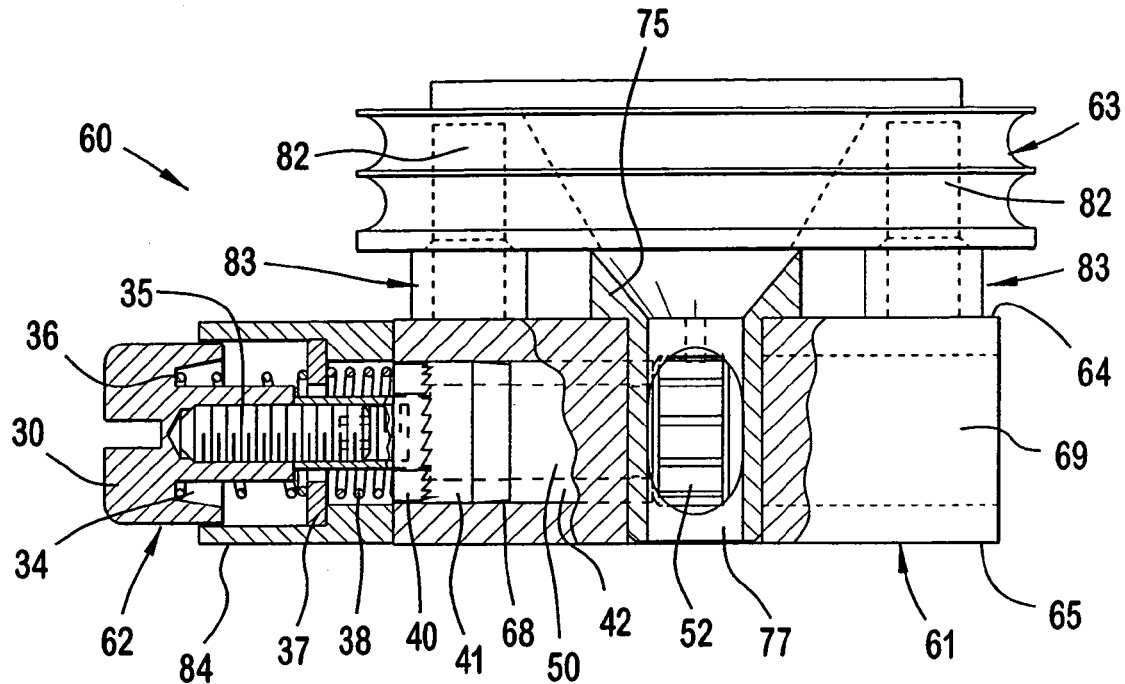
FIG. 10 is a cross-sectional side view of a second embodiment of a prosthetic attachment locking device according to the invention.
FIG. 11 is a schematic top view of the prosthetic attachment locking device of FIG. 10.
Figure 15:
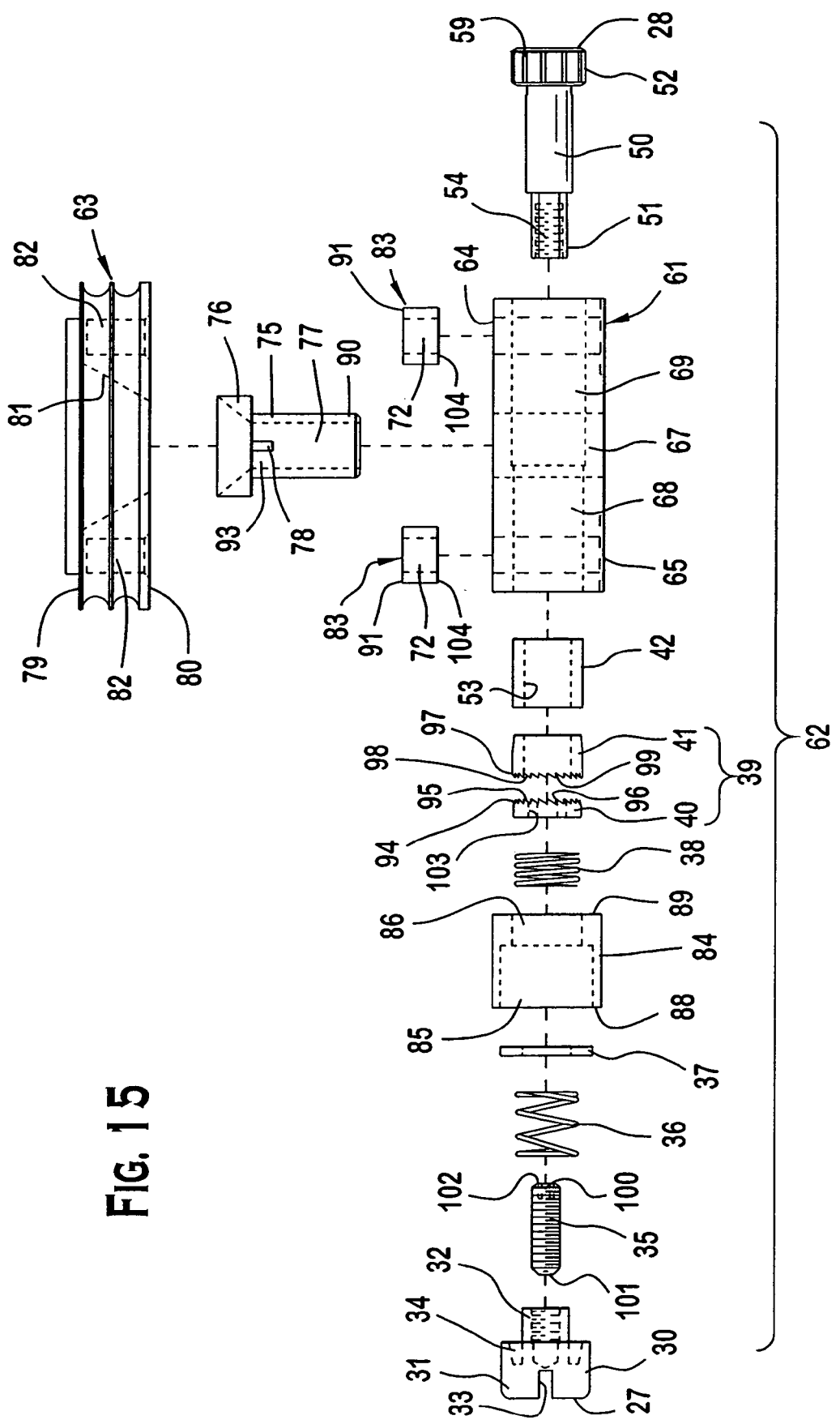
FIG. 15 is an exploded view of the prosthetic attachment locking device of FIG. 10.
Figure 16:
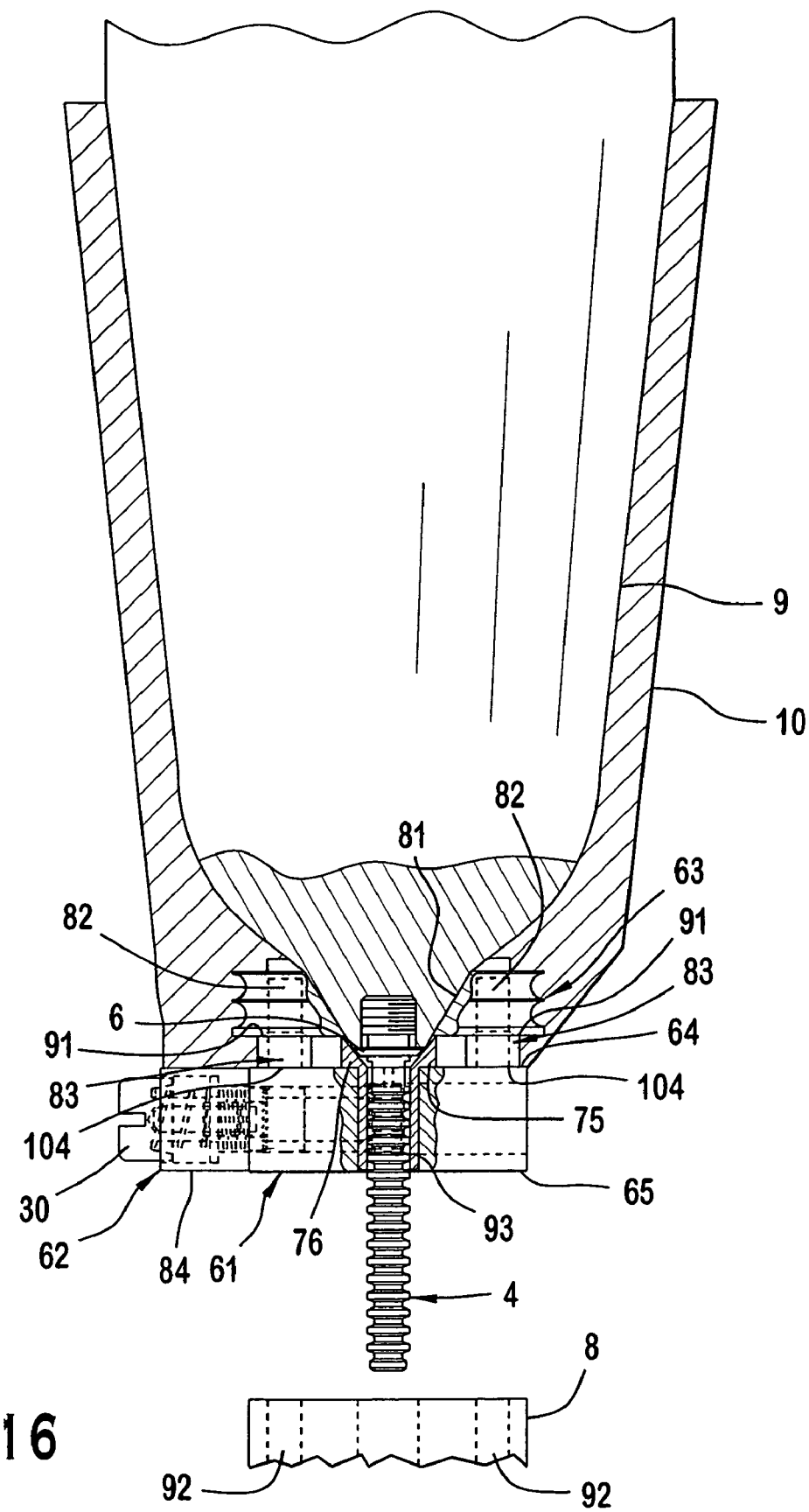
FIG. 16 is an exploded view of the prosthetic attachment locking device of FIG. 10 attached to a residual limb.

FIGS. 10–21 show a second embodiment of a prosthetic attachment locking device 60. Components of the second embodiment that are the same as components of the first embodiment will be identified with the same reference numerals and will not be described in greater detail hereafter. As shown in FIG. 10, the prosthetic attachment locking device 60 comprises a body 61, a locking mechanism 62, a socket adapter 63, hollow cylindrical spacers 83, and a ratcheted attachment pin 4 (FIG. 16). As shown in FIG. 12, the body 61 has side surfaces 66 extending between essentially planar first and second surfaces 64, 65. An axial hole 67 is formed in an approximate center of the body 61 and extends from the first surface 64 to the second surface 65. Extending from one of the side surfaces 66 of the body 61 toward the axial hole 67, is a clutch receiving recess 68. Adjacent to the clutch receiving recess 68 is a pawl receiving recess 69. The pawl receiving recess 69 has a diameter smaller than the clutch receiving recess 68 and extends from the clutch receiving recess 68 away from the axial hole 67 and through an opposing one of the side surfaces 66. As shown in FIG. 13, a portion of the clutch receiving recess 68 and the pawl receiving recess 69 communicate with the axial hole 67 to form a pawl receiving slot 87. Substantially adjacent to the axial hole 67 and formed on the first surface 14 is a dowel pin hole 73.

As shown in FIGS. 13 and 14, first and second sets of through-holes 70, 71 extend from the first surface 64 to the second surface 65. The first set of through-holes 70 is arranged around a perimeter of the body 61 at corners thereof and is threaded for receipt of a fastening means (not shown), such as a screw. The first set of through-holes 70 are arranged to form a universal pattern for attachment of the body 61 to a pylon 8 of a prosthetic limb (not shown), to be described later. The second set of through-holes 71 is arranged around a perimeter of the body 61. As shown in FIG. 14, on the second surface 65 of the body 61, each of the second set of through-holes 71 has a counter sink or counter bore 74 for receiving a head of a fastening means (not shown). The counter sink or counter bore 74 is formed such that the head of the fastening means (not shown) lies flush with the second surface 65 of the body 61 when received therein.

As shown in FIG. 15, the body 61 has a bushing 75. The bushing 75 has a stem 90 and an outwardly extending flange 76. An attachment pin receiving aperture 93 extends through the flange 76 and the stem 90. The stem 90 corresponds with the axial hole 67 and has a radial hole 77 that communicates with the attachment pin receiving aperture 93 and corresponds with the pawl receiving slot 87. A dowel pin 78 extends from the flange 76 toward the body 61 and corresponds with the dowel pin hole 73. The body 61 may be made from a high strength aluminum alloy for light weight and durability. The bushing 75 may be made of a high strength stainless alloy for durability and corrosive resistance.

As shown in FIG. 15, the socket adapter 63 has a residual limb receiving surface 79 and a body receiving surface 80. The residual limb receiving surface 79 has an outer surface 81 that tapers inward proximate the attachment pin receiving aperture 93 of the flange 76. A plurality of screw receiving apertures 82 that correspond with the second set of through-holes 71 extend from the body receiving surface 79 toward the residual limb receiving surface 79. As shown in FIG. 16, the socket adapter 63 may be laminated, thermo, or vacuum formed with a conventional socket 10.

As shown in FIG. 15, the hollow cylindrical spacers 83 have essentially planar first and second faces 91, 104. A screw receiving recess 72 that corresponds with the second set of through-holes 71 extends between the first and second faces 91, 104.

As shown in FIG. 15, the locking mechanism 62 is essentially cylindrical in shape and has a first end 27 and a second end 28. The locking mechanism 62 may be made from a material such as a high strength aluminum alloy for light weight and durability. The first end 27 of the locking mechanism 3 includes a release button 30, a screw 35, a first compression spring 36, a spacer 37, a sleeve 84, a second compression spring 38, a ratchet 39 consisting of a driving portion 40 and a stationary portion 41, and a one-way clutch 42. The sleeve 84 has a first face 88 and a second face 89. A button receiving recess 85 extends from the first face 88 toward the second face 89. A second compression spring receiving recess 86 extends from the button receiving recess 85 through the second face 89 and has a smaller diameter than the button receiving recess 85. As shown in FIG. 10, the spacer 37 is arranged in the button receiving recess 85. The second compression spring 38 is arranged in the second compression spring receiving recess 86 so that the second compression spring 38 is arranged adjacent to the spacer 37. The one-way clutch 42 and the ratchet 39 are arranged in the clutch receiving recess 68 of the body 61 so that the driving portion 40 is arranged adjacent to the second compression spring 38 and the stationary portion 41 is arranged adjacent to the driving portion 40. The stationary portion 41 may be integrally formed with the clutch receiving recess 68. In the alternative, the driving portion 40 may be arranged in the second compression spring receiving recess 86 of the sleeve 84. Additionally, the second compression spring 38 and the spacer 37 could be eliminated, and the first compression spring 36 could be arranged adjacent to the driving portion 40. The second end 28 of the locking mechanism 3 includes a central axle 50 with a pawl 52.

The assembly and operation of the second embodiment of the prosthetic attachment locking device 60 will now be described in greater detail with reference to FIGS. 10, 11, and 16. As shown in FIG. 10, to assemble the locking mechanism 62, the stem 90 of the bushing 75 is inserted into the axle hole 67 so that the dowel pin 78 is received in the dowel pin hole 73 and the radial hole 77 is aligned with the pawl receiving slot 87. The attachment end 51 of the central axle 50 is inserted into the pawl receiving recess 69 until the attachment end 51 is received in the driving portion 40 and the pawl 52 is received in the radial hole 77. The second face 89 of the sleeve 84 is positioned to abut the side surface 66 of the body 61. The release button 30 is inserted into the button receiving recess 85 so that the screw 35, which is encompassed with the first compression spring 36, is received by the spacer 37 and the second compression spring 38. The screw 35 is secured in the screw receiving recess 54 of the attachment end 51 by rotating the release button 30 either manually or with a tool (not shown) positioned in the recess 33. The release button 30, the sleeve 84, and the central axle 50 are thereby attached. In the assembled state, the release button 30 is biased by the first compression spring 36 toward the first end 27, and the driving portion 40 is biased by the second compression spring 38 toward the second end 28 and against the stationary portion 41.

As shown in FIGS. 11 and 16, the first surface 64 of the body 61 is positioned adjacent to the body receiving surface 80 of the socket adapter 63, which is integrally formed with the conventional socket 10. The first faces 91 of the hollow cylindrical spacers 83 are aligned with the screw receiving apertures 82 of the socket adapter 63. The second faces 104 of the hollow cylindrical spacers 83 are aligned with the second set of through-holes 71 of the body 61 and are positioned against the first surface 64. Fastening means (not shown), such as screws, are received in the second set of through-holes 71 from the second surface 65 of the body 61 such that the heads of the fastening means (not shown) are received in the counter sink or counter bore surfaces 74. The fastening means (not shown) extends thought the body 61, the hollow cylindrical spacers 83, and into the socket adapter 63 to attach the socket adapter 63 to the body 61.

The second surface 65 of the body 61 is positioned adjacent to the pylon 8 of the prosthetic limb (not shown). Fastening means (not shown), such as screws, that extend from apertures 92 in the pylon 8 are received in the first set of through-holes 70 in the body 61. The fastening means (not shown) attach the pylon 8 and the prosthetic limb (not shown) to the body 2.

The conventional socket 10, which has been laminated or vacuum formed with the socket adapter 63, is fitted over a liner 9 that covers a residual limb (not shown). As the conventional socket 10 is positioned over the liner 9, the attachment pin 4, which extends from the liner 9, is guided into the attachment pin receiving aperture 93 by the outer surface 81 of the socket adapter 63 and the flange 76 of the bushing 75. As the attachment pin 4 is received in the attachment pin receiving aperture 93, the ratcheted teeth 11 of the attachment pin 4 engage the teeth 59 of the pawl 52 at the pawl receiving slot 87 and cause the central axle 50 to rotate within the one-way clutch 42. The rotation of the central axle 50 causes the driving portion 40 to rotate with the attachment end 51. As the driving portion 40 rotates, the ratchet 39 locks in discrete positions, and the driving teeth 94 engage the stationary teeth 97 to cause an audible clicking sound. The attachment pin 4 is inserted until the lip 6 of the attachment pin 4 is positioned adjacent to the attachment pin receiving aperture 93 and a distal end of the attachment pin 4 is received in the pylon 8 of the prosthetic limb (not shown) to secure the residual limb (not shown) to the prosthetic limb (not shown).

To detach the liner 9 of the residual limb (not shown) from the prosthetic limb (not shown), the head 31 of the release button 30 is pressed toward the body 2 and pushes against the bias of the first compression spring 36. As the head 31 is received in the button receiving recess 85 of the sleeve 84, the head 31 displaces the central axle 50 and the pawl 52. The second face 89 holds the sleeve 84 in position while the central axle 50 and pawl 52 are being displaced. The pawl 52 is displaced beyond the pawl receiving slot 87 so that the attachment pin 4 is released from the pawl 52 and resultantly may be removed from the attachment pin receiving aperture 93 to detach the liner 9 of the residual limb (not shown) from the pylon 8 of the prosthetic limb (not shown).

Because the attachment pin 4 is secured in the body 2 by the driving portion 40 engaging with the stationary portion 41 and the central axle 50 engaging with the one-way clutch 42, the attachment pin 4 is dually locked in the body 2 and play between the attachment pin 2 and the pawl 52 is reduced. Additionally, because the ratcheted teeth 11 of the attachment pin 4 are substantially flat, the teeth 59 of the pawl 52 mesh with the ratcheted teeth 11 of the attachment pin 4 to reduce play between the ratcheted teeth 11 and the teeth 59. Further, the hollow cylindrical spacers 83 arranged between the body 61 and the socket adapter 63 eliminate the uneven distribution of torque that occurs with a conventional socket adapter.

The body 61 and the socket adapter 63 of the second embodiment of the prosthetic locking device 60 may alternatively be formed as shown in FIGS. 17–21. Components of the alternate embodiments of the body 61' and the socket adapter 63' that are the same as components of the body 61 and the socket adapter 63 will be identified with the same reference numerals and will not be described in greater detail hereafter.

Figure 17:
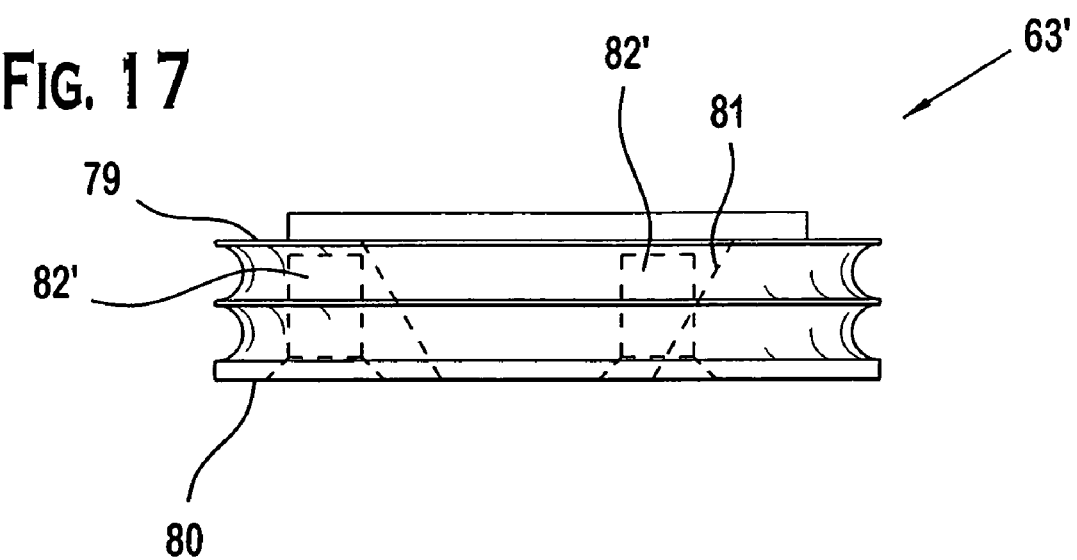
FIG. 17 is a side schematic view of an alternate embodiment of the socket adapter of FIG. 10.
Figure 18:
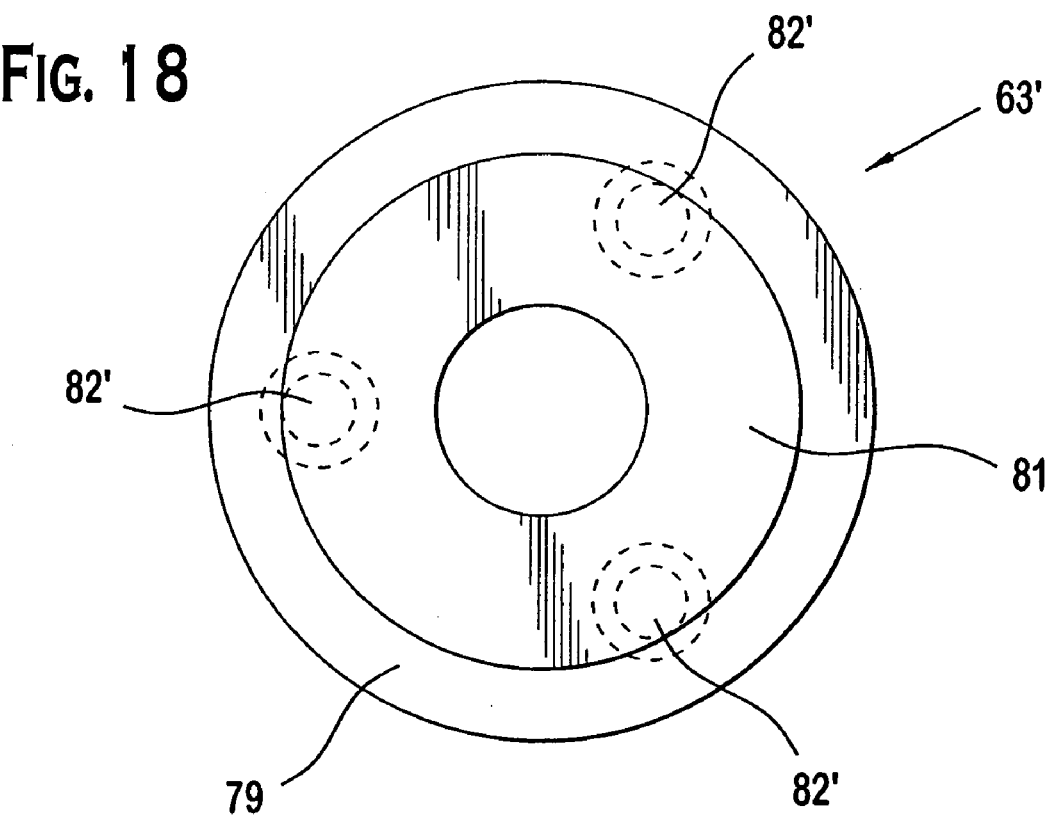
FIG. 18 is a top schematic view of the socket adapter of FIG. 17.
Figure 19:
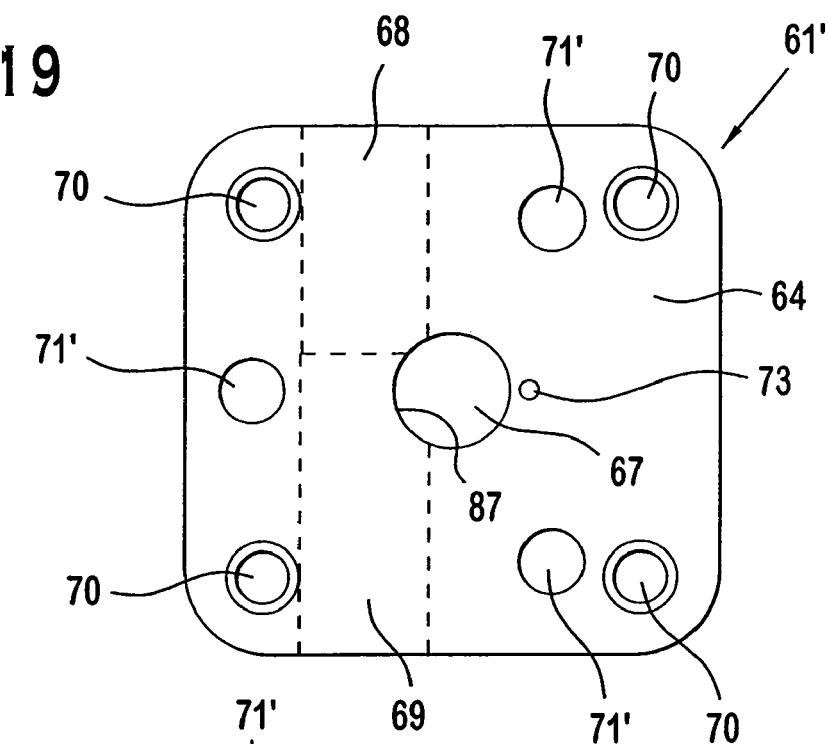
FIG. 19 is a top schematic view of an alternate embodiment of the body of FIG. 10.
Figure 20:
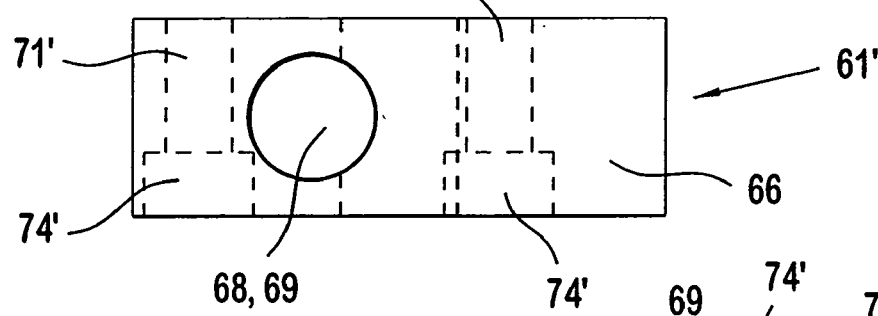
FIG. 20 is a side schematic view of the body of FIG. 19.
Figure 21:
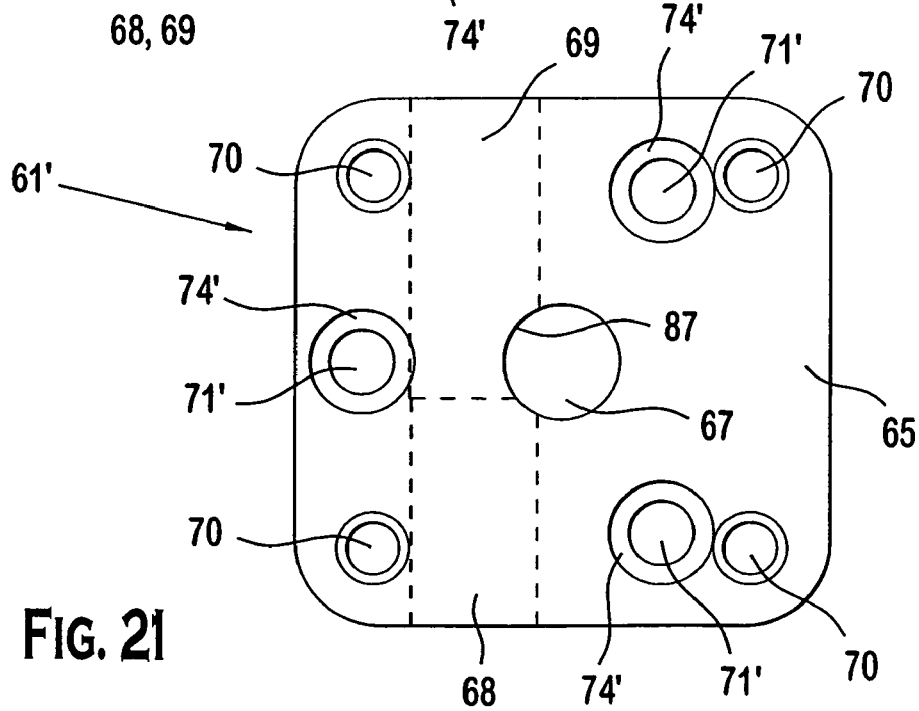
FIG. 21 is a bottom schematic view of the body of FIG. 19.

As shown in FIGS. 19–21, the body 61' is substantially the same as the body 61 except the second set of through-holes 71' is arranged in a substantially triangular configuration. On the second surface 65 of the body 61', each of the second set of through-holes 71' has a counter sink or counter bore 74' for receiving a head of a fastening means (not shown). The counter sink or counter bore 74' is formed such that the head of the fastening means (not shown) lies flush with the second surface 65 of the body 61' when received therein. As shown in FIGS. 17–18, the socket adapter 63' is substantially the same as the socket adapter 63 except the screw receiving apertures 82' correspond with the second set of through-holes 71'.

Because the assembly and operation of the alternate embodiments of the body 61' and the socket adapter 63' are substantially the same as the assembly and operation of the body 61 and the socket adapter 63, their assembly and operation will not be described in greater detail hereafter. This configuration, however, further helps to compensate for irregularities in the body receiving surface 80.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. A prosthetic attachment locking device, comprising:
a body having an axle hole that extends between a surface and a second a surface;
a locking mechnanism having a central axle with a pawl that communicate with the axial hole, the pawl being displaceable to selectively engage with an attachment pin received in the axial hole;
the locking mechanism having a one-way clutch and a ratchet, the one-way clutch and the ratchet being formed to receive the central axle and permit one-way rotation of the pawl; and
the ratchet including a driving portion that engages with a stationary portion.

2. The device of claim 1, wherein the one-way clutch rotatably mounts the centering axle.

3. The device of claim 1, wherein the non-rotatably mounts the centering axle.

4. The device of claim 1, wherein the locking mechanism includes a release bottom attached to the central axle and biased by a first compression spring.

5. The device of claim 4, wherein the release button includes an undercut for receiving the first compression spring.

6. The device of claim 1, wherein the stationary portion is integrally formed with the body.

7. The device of claim 1, wherein the stationary portion is integrally formed with a sleeve of the lacking mechanism.

8. The device of claim 1, wherein the locking mechanism includes a second compression spring that biases the driving portion into engagement with the stationary portion.

9. The device of claim 1, wherein the body is formed from a plastic material.

10. The device of claim 1, wherein the body is formed from an aluminum alloy.

11. The device of claim 1, wherein the ratchet and the one-way clutch are arranged in a sleeve.

12. The device of claim 11 wherein the body includes a locking mechanism that engages the sleeve to retain the sleeve within the body.

13. The device of claim 1, wherein the first surface of the body is formed with an integral socket adapter.

14. The device of claim 1, further comprising a socket adapter and hollow cylindrical spacers, the hollow cylindrical spacers being arranged between the body and the socket adapter.

15. The device of claim 1, further comprising a socket adapter having screw receiving apertures, the screw receiving apertures corresponding to a second set of through-holes formed in the body.

16. The device of claim 15, wherein the body has no more than three of the through-holes and the through-holes are arranged in a substantially triangular configuration.

17. The device of claim 1, wherein the attachment pin includes a pin body with a plurality of ratcheted teeth, the ratcheted teeth having a substantially flat engaging surface and a depth from an outer circumference to the pin body of approximately ⅟₁₆ of an inch.

18. The device of claim 1, wherein the body includes a bushing that is receivable in the axial hole, the bushing having an outwardly extending flange for guiding the attachment pin into the body.

19. The device of claim 1, wherein the one-way clutch acts as a bearing for the central axle.

20. A locking mechanism for a prosthetic attachment locking device, comprising:
a central axle having a pawl;
a one-way clutch rotatably mounting the central axle that permits one-way rotation of the central axle;
a ratchet mounting the central axle that permits one-way rotation of the central axle, the ratchet including a driving portion that engages with a stationary portion, the driving portion non-rotatably mounting the central axle; and
a release button attached to the central axle and biased by a first compression spring, the release button being moveable to displace the central axle and the pawl.

21. The locking mechanism of claim 20, wherein the first compression spring biases the driving portion into engagement with the stationary portion.

22. The locking mechanism of claim 20, further comprising a sleeve that receives the central axle, the one-way clutch, and the ratchet.

23. The locking mechanism of claim 22, wherein the stationary portion is integrally formed with the sleeve.

24. The locking mechanism of claim 22, wherein the sleeve has a threaded outer surface.

25. The locking mechanism of claim 20, wherein the release button has an undercut for receiving the first compression spring.

26. The locking mechanism of claim 20, wherein the one-way clutch acts as a bearing for the central axle.

27. The locking mechanism of claim 20, further comprising a second compression spring for further biasing the release button.

* * * * *

UNITED STATES PATENT AND TRADEMARK OFFICE
CERTIFICATE OF CORRECTION

PATENT NO. : 7,108,722 B2 Page 1 of 1
APPLICATION NO. : 10/810519
DATED : September 19, 2006
INVENTOR(S) : Chris L. Wagman It is certified that error appears in the above-identified patent and that said Letters Patent is hereby corrected as shown below:

Column 9:
In claim 1, line 2, "axle" should read --axial--.

Column 9:
In claim 1, line 2, "a surface" should read --a first surface--.

Column 9:
In claim 1, line 3, "second a surface" should read --second surface--.

Column 9:
In claim 1, line 5, "communicate" should read --communicates--.

Column 9:
In claim 3, line 1, "the non-rotatably" should read --the driving portion non-rotatably--.

Column 10:
In claim 7, line 2, "lacking" should read --locking--.

Signed and Sealed this

Twelfth Day of December, 2006

JON W. DUDAS
*Director of the United States Patent and Trademark Office*